US008766000B2

(12) United States Patent
Lomel et al.

(10) Patent No.: US 8,766,000 B2
(45) Date of Patent: Jul. 1, 2014

(54) CONTINUOUS METHOD FOR MANUFACTURING BETAINE AQUEOUS SOLUTION

(75) Inventors: Sébastien Lomel, Saint Just Chaleyssin (FR); Pascal Pitiot, Lyons (FR); Thierry Gisbert, Miribel (FR)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 13/636,588

(22) PCT Filed: Mar. 23, 2011

(86) PCT No.: PCT/FR2011/050611
§ 371 (c)(1),
(2), (4) Date: Nov. 30, 2012

(87) PCT Pub. No.: WO2011/117535
PCT Pub. Date: Sep. 29, 2011

(65) Prior Publication Data
US 2013/0066108 A1    Mar. 14, 2013

(30) Foreign Application Priority Data
Mar. 23, 2010  (FR) .................... 10 52079

(51) Int. Cl.
*C07C 205/00* (2006.01)
*C07C 229/00* (2006.01)

(52) U.S. Cl.
USPC ............................................. 562/553; 562/575

(58) Field of Classification Search
None
See application file for complete search history.

(56) References Cited

U.S. PATENT DOCUMENTS

| 4,497,825 | A |   | 2/1985 | Bade |         |
|-----------|---|---|--------|------|---------|
| 5,292,942 | A | * | 3/1994 | Aigner et al. | 562/575 |
| 2010/0267986 | A1 | * | 10/2010 | Paradies et al. | 562/554 |

OTHER PUBLICATIONS

"Reactor Types and Their Industrial Applications" in Ullmann's Encyclopedia of Industrial Chemistry, Klaus-Dieter Henkel, pp. 293-327, Published Online : Jun. 15, 2000, DOI: 10.1002/14356007.b04_87.*
International search report and written opinion for application No. PCT/FR2011/050611 dated May 20, 2011.

* cited by examiner

*Primary Examiner* — Karl J Puttlitz
(74) *Attorney, Agent, or Firm* — Patterson & Sheridan, L.L.P.

(57) ABSTRACT

The present invention relates to a method for continuously preparing a betaine aqueous solution, including the reaction of an amine with an ω-halocarboxylic acid, in the presence of water and a base. Said method is characterized in that it is carried out in a device consisting of at least two consecutive reactors (R1) and (R2), the reactor (R2) being a tubular reactor.

24 Claims, 3 Drawing Sheets

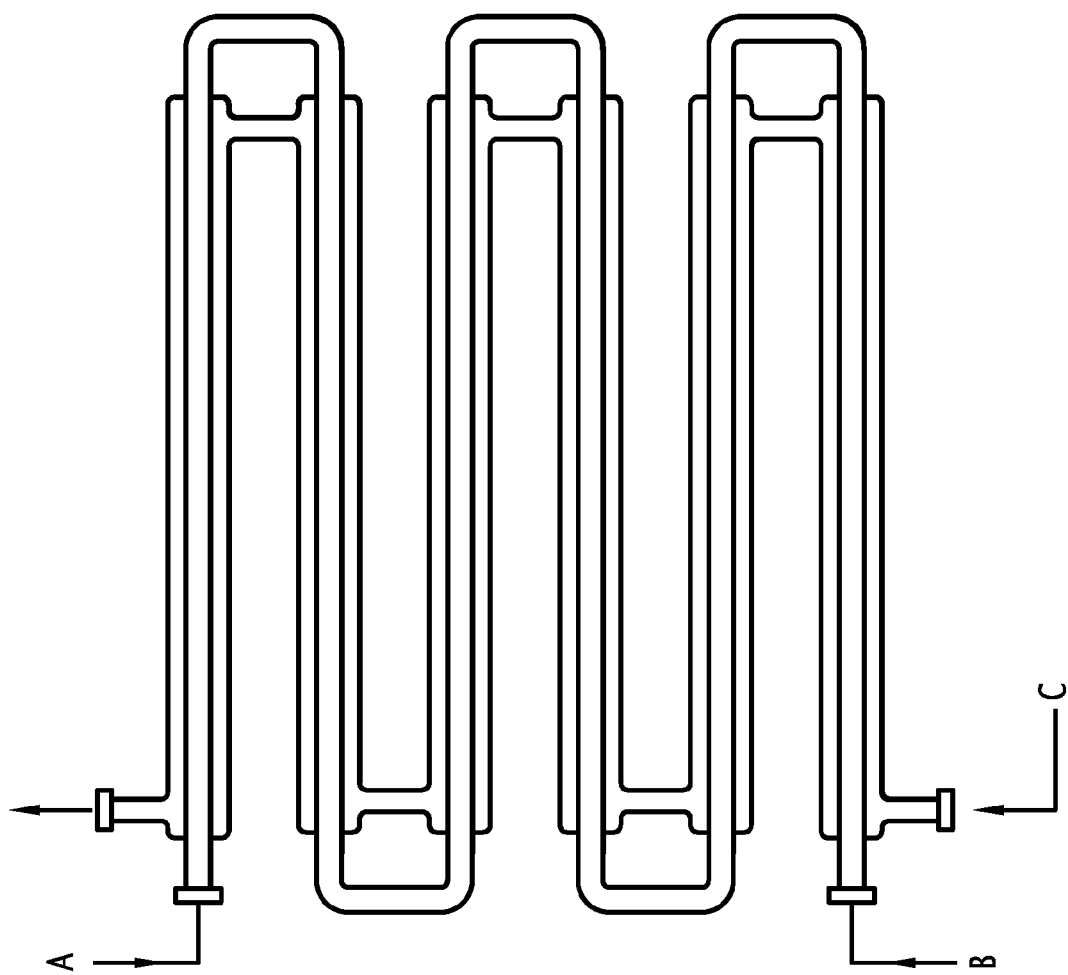

CONTINUOUS METHOD FOR MANUFACTURING BETAINE AQUEOUS SOLUTION

The present invention relates to a continuous method for manufacturing betaine aqueous solutions.

Glyphosate (N-(phosphonomethyl)glycine, $C_3H_8NO_5P$) is an herbicide well known by those skilled in the art. Different formulations exist comprising this herbicide. It is in particular especially interesting to have ready-to-use compositions available to end users (in particular farmers).

This herbicide is in particular presented in the form of compositions comprising glyphosate, water, and at least one surfactant.

Currently, compositions are essentially known comprising glyphosate and surfactants from the ethoxylated fatty amine family. However, these surfactants are known to be eco-toxic, irritating, and weakly biodegradable.

Thus, these surfactants are now replaced by other surfactants, in particular by quaternary ammonium compounds from the betaine family.

The preparation of betaine aqueous solutions by reacting tertiary amines with an ω-halocarboxylic acid and a base in an aqueous phase is well known by those skilled in the art, and in particular from U.S. Pat. No. 3,819,539 and U.S. Pat. No. 4,497,825.

The resulting aqueous solutions essentially comprise betaine, the formed alkali metal halogen salt, and water.

These solutions are usable in that condition. However, if they contain too high a residual quantity of amine, the properties of these solutions are lessened.

U.S. Pat. No. 5,292,942 describes a method for preparing betaine aqueous solutions using a continuous method in at least two agitated reactors. However, this method is a long method with excessive residence times of the reagents, exceeding 10 hours, which does not make it possible to recover the final product quickly. The agitated reactors adopted in this patent are characterized by a spread out distribution of the residence time, which requires, when there is a change in production in terms of flow rates, nature of the produced betaine or others, waiting at least three times the residence time for each reactor to achieve an admissible quality of the product. Also, in the cited patent, it is necessary to wait at least 50 hours to produce a premium product, the production during the time between campaigns being downgraded and destroyed. Adopting long residence times leads, for a given flow rate, to sizing units with large volumes, which cannot be transported, and which are expensive from an investment perspective.

The present invention aims to provide a method for preparing betaine aqueous solutions having reduced residence times.

The present invention also aims to provide a preparation method that is flexible and compact, making it possible to obtain betaine aqueous solutions of constant quality without a step for correcting the quality.

The present invention also aims to provide a method for preparing betaine aqueous solutions characterized by the possibility of carrying out steps for continuously formulating the betaine and thus doing away with any discontinuous subsequent mixing step, as well as storage.

The present invention also aims to provide a quick and easy method for preparing betaine aqueous solutions with a high betaine concentration.

The present invention relates to a continuous method for preparing a betaine aqueous solution with the following formula (I):

$$R-\overset{R_2}{\underset{R_1}{N^+}}-(CH_2)_n-\overset{O}{\underset{O^-}{C}} \quad (I)$$

wherein:

n is equal to 1, 2 or 3;

$R_1$ represents a linear or branched alkyl group, comprising from 1 to 3 carbon atoms, preferably a methyl group;

$R_2$ represents a linear or branched alkyl group, comprising from 1 to 3 carbon atoms, preferably a methyl group;

R represents:
either a linear or branched hydrocarbonaceous chain, preferably an alkyl group, comprising from 3 to 30 carbon atoms, and in particular from 3 to 20 carbon atoms;
or an -A-NH—CO—$R_3$ group,
$R_3$ representing a linear or branched hydrocarbonaceous chain, preferably an alkyl group, comprising from 3 to 30 carbon atoms, and in particular from 3 to 20 carbon atoms; and
A representing a linear or branched divalent hydrocarbonaceous group comprising from 1 to 6 carbon atoms, possibly substituted by a hydroxyl group, and preferably chosen from among the groups: —$CH_2$—$CH_2$—$CH_2$— and —$CH_2$—CHOH—$CH_2$—;

comprising the reaction of an anime of formula $NRR^1R^2$, R, $R^1$ and $R^2$ being as defined above, with an ω-halocarboxylic acid having formula X—$(CH_2)_n$—COOH, X representing a halogen atom and n being as defined above, in the presence of water and a base, in particular an alkali metal hydroxide, and more particularly KOH or NaOH, characterized in that said method is carried out in a device made up of at least two consecutive reactors ($R^1$) and ($R^2$), the reactor ($R^2$) being a tubular reactor.

According to the present invention, the term "hydrocarbonaceous chain" designates a group comprising carbon atoms and hydrogen atoms, and more particularly designates the alkyl groups.

According to the present invention, the "alkyl" radicals represent saturated hydrocarbonaceous radicals, in a straight or branched chain, for example comprising from 1 to 3 carbon atoms, or from 3 to 30, preferably from 3 to 20, carbon atoms (they can typically be represented by the formula $C_nH_{2n+1}$, n representing the number of carbon atoms). Examples in particular include, when they are linear, the methyl, ethyl, propyl, butyl, pentyl, hexyl, octyl, nonyl and decyl radicals. Examples in particular include, when they are branched or substituted by one or more alkyl radicals, the isopropyl, tert-butyl, 2-ethylhexyl, 2-methylbutyl, 2-methylpentyl, 1-methylpentyl and 3-methylheptyl radicals.

In formula (I), the $R_1$ and $R_2$ groups can be identical or different.

Preferably, in formula (I), R represents an alkyl group comprising 12 or 14 carbon atoms.

Among the halogen atoms, to define X, examples more particularly include fluorine, chlorine, bromine and iodine atoms. Preferably, X represents a chlorine atom.

The method according to the present invention therefore consists of preparing betaine aqueous solutions, i.e. solutions comprising at least betaine (meeting formula (I) above) and water.

Contrary to the methods often used to prepare betaine solutions, which are discontinuous methods (or batch methods), the inventive method is in fact continuous. Thus, the method according to the invention consists of carrying out all of the steps continuously.

For example, the reagents, i.e. in particular the amine and the acid, are introduced into the device continuously, and not all at once as in the context of a discontinuous method.

The method according to the present invention in particular consists of reacting the amine of formula (I) with an ω-halocarboxylic acid, this reaction being well known by those skilled in the art.

This reaction is done in the presence of a base that will make it possible to find appropriate pH conditions, and therefore the ω-halocarboxylic acid will be in carboxylate form.

The bases used for the reaction between the amine and the acid in particular include KOH or NaOH, or any strong base such as LiOH, CsOH or $Ca(OH)_2$.

Preferably, the base used is potassium hydroxide.

The amine used in the context of the inventive method can assume the form of a mixture of several amines.

Likewise, the acid used in the context of the inventive method can assume the form of a mixture of several acids.

The device implemented in the context of the present invention therefore comprises at least two reactors, and preferably two reactors (R1) and (R2).

These two consecutive reactors are arranged cascading, i.e. one following the other. In this way, the outlet of the reactor (R1) is connected to the inlet of the reactor (R2).

The reactor (R1), situated upstream, can be of any nature, i.e. an agitated reactor or a tubular reactor, and the reactor (R2) is a tubular reactor.

According to the inventive method, the amine and the ω-halocarboxylic acid are introduced continuously into the reactor (R1) and react together to form the betaine aqueous solution recoverable at the outlet of the reactor (R2). Likewise, the reactive mixture (M), recovered at the outlet of the reactor (R1), is introduced continuously, i.e. during the advancement of the reaction, at the inlet of the reactor (R2).

According to one preferred embodiment, the method according to the present invention comprises:

a) a step for introducing water, base, amine, and the ω-halocarboxylic acid at the inlet of the reactor (R1), b) a reaction step between the amine and the ω-halocarboxylic acid in the reactor (R1) to obtain, at the outlet of the reactor (R1), an aqueous reactive mixture (M) comprising betaine, amine and ω-halocarboxylic acid;

c) a step for introducing the aqueous reactive mixture (M) at the inlet of the reactor (R2), to continue the reaction between the amine and the ω-halocarboxylic acid; and d) a step for recovering a betaine aqueous solution (M') at the outlet of the reactor (R2) comprising at least 30 wt % of betaine; less than 2.5 wt %, preferably less than 1.65 wt %, of amine; and less than 1.5 wt %, in particular less than 1 wt %, and preferably less than 0.7 wt %, of acid.

The reactive mixture (M) comprises a majority of betaine, and preferably at a rate of more than 30 wt % in relation to the total weight of the mixture. It also comprises the residual amine and ω-halocarboxylic acid. The amine is present in the mixture (M) at a rate of 3 wt % to 6 wt %, and preferably 5 wt %, and the acid is present at a rate of 2 wt % to 5 wt %, preferably 2 wt %.

This mixture also contains a number of products resulting from secondary reactions, and in particular glycolic acid.

According to one particular embodiment, the mixture (M) comprises 5 wt % of amine, 2 wt % of acid, 1 wt % of glycolic acid and 26 wt % of betaine.

The reactive mixture (M') comprises betaine at a rate of at least 30 wt %, preferably from 30 wt % to 50 wt %. According to one particular embodiment, the quantity of betaine in this mixture (M') is approximately 34 wt % in relation to the total weight of the composition.

All of the steps of the method are carried out continuously.

During step a), the water can also be introduced via dilution of the acid. In that case, this introduction step is done by means of three inlet flows, i.e. amine, diluted acid, and base inlets.

The aqueous reactive mixture (M), obtained at the outlet of the reactor (R1), and introduced into the reactor (R2), comprises water, amine of formula (I), ω-halocarboxylic acid and the betaine formed in the reactor (R1).

This reactive mixture is not usable in that state, due to the still-excessive quantities of residual amine and acid.

Depending on the advancement of the reaction, the betaine concentration increases over time in the reactor (R2).

According to one particularly preferred embodiment, during step a) of the inventive method, one introduces the amine with the base on the one hand, and the acid with the water on the other hand.

Preferably, the amine and the base are mixed and introduced together, for example via mixers or micromixers.

Preferably, the acid and the water are mixed and introduced together, for example via mixers or micromixers.

This embodiment makes it possible to avoid the exothermic neutralization reaction that occurs between the acid and the base. In fact, this exothermic reaction can cause crystallization problems related to the low solubility of the salt as a function of the temperature. This embodiment also makes it possible to avoid large quantities of secondary products whereof the reactions are activated by the temperature increase.

According to one particularly preferred embodiment, the method according to the present invention may comprise an additional step b'), consisting of adding base into the reactive mixture (M) at the outlet of the reactor (R1) and before introducing said mixture into the reactor (R2). This step is therefore carried out between step b) and step c). This addition of base can also be done directly in the reactor (R2).

This base can be the same as the base used in the reactor (R1), but it may also be different.

This additional step thus makes it possible to monitor the pH during the reaction in (R1) and (R2), and therefore to increase the reaction speed and limit the secondary reactions. Preferably, the pH at the outlet of the reactor (R1) is above 7.

The inventive method also has the advantage of not requiring an additional step to add hydrochloric acid into the solution (M'), inasmuch as the pH of the medium at the outlet of the reactor is comprised between 7 and 8.

The addition of the exact quantity of base necessary (by adjustment owing to the secondary injection of base between (R1) and (R2)) avoids the need to correct the pH at the outlet of (R2), the latter being comprised between 7 and 8. As a comparison, in a batch reactor, the pH before the addition of HCl is approximately 10-11.

Another preferred embodiment of the invention consists of reinjecting a portion of the betaine aqueous solution (M') at the inlet of the reactor (R1), mixed with the amine and the base. Thus, it is preferably possible to recover betaine aqueous solution (M') at the outlet of the reactor (R2) to reintroduce it at the inlet of the reactor (R1). Preferably, 1 wt % of the solution (M') is reinjected in relation to the total flow rate.

This embodiment makes it possible to facilitate the solubilization of the amine and makes it possible to avoid decanting of the reactive medium, which is initially diphasic.

According to another embodiment of the method, the outlet of the reactor (R2) can be connected to one or more mixers, in series or in parallel, allowing the continuous addition and mixing of additives such as water, glycerin, propylene, sorbitol, glycols, any non-reducing sugar, anti-foaming agents or any other liquid additive necessary for the formulation, or mixtures thereof, in order to prepare betaine-based in-line formulations.

The inventive method makes it possible to obtain betaine aqueous solutions that can be used in that state, i.e. that can be used directly to prepare formulations, in particular for formulations of herbicide compositions, and more particularly for glyphosate-based formulations.

To that end, the device implemented in the context of the present invention can be connected to mixers comprising the appropriate compounds to prepare the desired formulations. Thus, the outlet of the reactor (R2) can for example be connected to a mixer comprising water and a mixer comprising glycerin.

The formulations can then be delivered directly to the users in trucks. This avoids the use of different facilities. It is thus possible to connect the inventive device directly to the truck that will be used to deliver the formulation to the end user.

The formulations prepared from aqueous solutions obtained according to the inventive method can also comprise other surfactants, anti-foaming agents, solvents, preferably water-miscible solvents.

Preferably, the temperature inside the reactor (R1) is comprised between 80° C. and 110° C., preferably 90° C. to 100° C., and preferably equal to approximately 95° C.

The choice of these temperature ranges results from a compromise between quickly promoting the primary reaction while trying to limit the secondary reactions first.

Preferably, the temperature inside the reactor (R2) is comprised from 95° C. to 110° C., preferably from 100° C. to 105° C., and preferably equal to approximately 105° C.

The temperature is increased in (R2) this time so as to favor the secondary reaction, while also accelerating the primary reaction, the aim in fine being to be within the specifications for the residual acid and amine, i.e. within the desired content levels in acid and amine in the final betaine aqueous solution.

Preferably, the pressure inside the reactor (R2) is comprised from 1 to 10 bars, preferably 1.5 bars to 5 bars, and preferably from 2 to 3 bars.

The pressure is chosen so that the boiling temperature of the reactive medium is higher than the working temperature, with the result that the medium remains liquid and homogenous. The pressure can also be chosen so that it is above the saturation vapor pressure of the medium at the working temperature.

According to one particularly preferred embodiment, the reactor (R1) is a tubular reactor.

The method according to the present invention is therefore preferably carried out in a device made up of two tubular reactors (R1) and (R2).

According to one preferred embodiment of the inventive method, the residence time of the amine and the acid in the reactor (R1) is comprised from 30 minutes to 5 hours, preferably 30 minutes to 3 hours, and preferably 40 minutes to 80 minutes.

According to one preferred embodiment of the inventive method, the residence time of the amine and the acid in the reactor (R2) is from 30 minutes to 5 hours, preferably from 30 minutes to 3 hours, and preferably from 40 minutes to 120 minutes.

Particularly advantageously, the acid used in the context of the inventive preparation method is monochloroacetic acid.

Particularly advantageously, the amine used in the context of the inventive preparation method is lauryldimethylamine.

Thus, a particularly advantageous method consists of reacting lauryldimethylamine with monochloroacetic acid in the presence of potassium hydroxide and water in a device made up of two tubular reactors.

The reagents are introduced in (3) into the reactor (1) and the reactive mixture (M) formed is recovered in (4) at the outlet of the reactor (1) to be reinjected into the reactor (2).

Figure 1:
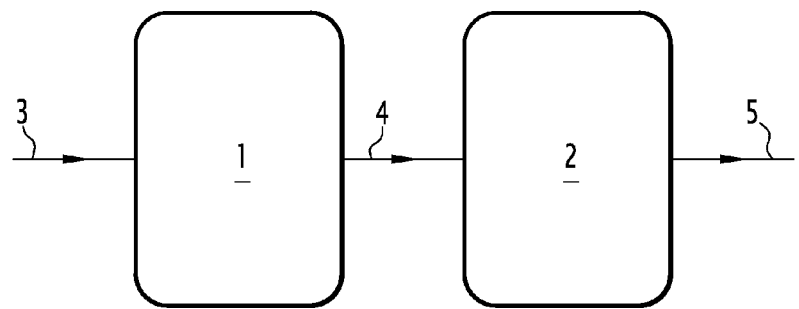
FIG. 1 shows a device made up of two reactors (1) and (2) arranged in series, i.e. connected to each other. The outlet of the reactor (1) is connected by means of (4) to the inlet of the reactor (2). At the outlet (5) of the reactor (2), the betaine aqueous solution can be recovered according to the inventive method. The outlet (5) can, if necessary, either be directly connected to means designed to load trucks for the delivery of said solutions, or can be connected to means designed to prepare betaine aqueous solution-based formulations (e.g. mixers).
Figure 2:
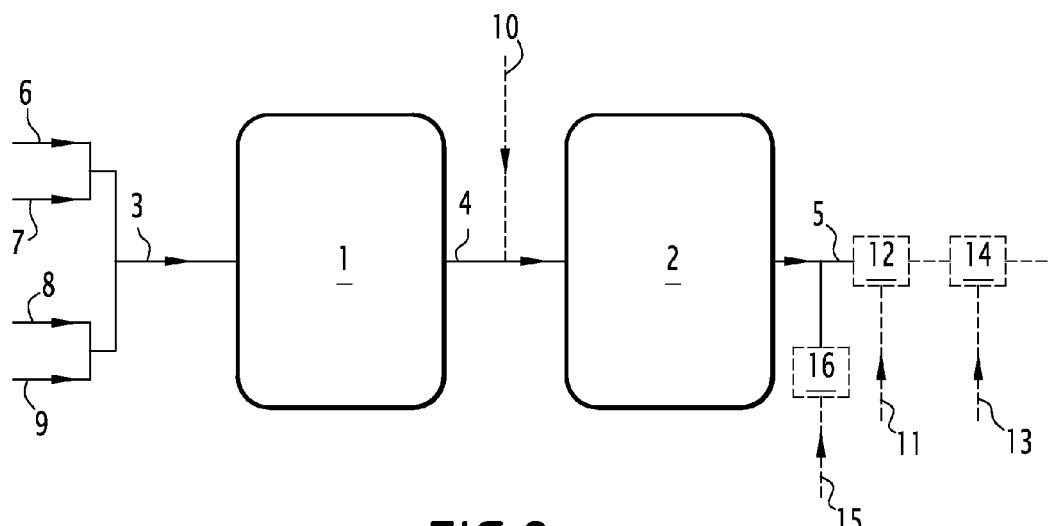

FIG. 2 shows an alternative of the device of FIG. 1.

This device is made up of two reactors (1) and (2) connected to each other by (4) (the outlet of the reactor (1) being connected to the inlet of the reactor (2)). The reagents are introduced at the inlet (3) of the reactor (1). The acid (6) and the water (7) are introduced together on the one hand, and the amine (8) and the base (9) on the other.

The outlet of the reactor (2) is connected to one or more mixers (12, 14, 16) in order to prepare formulations comprising betaine aqueous solutions (5) and other compounds (11, 13, 15).

This device also comprises an intermediate base addition (10) between the outlet of the reactor (1) and the inlet of the reactor (2).

Figure 3:
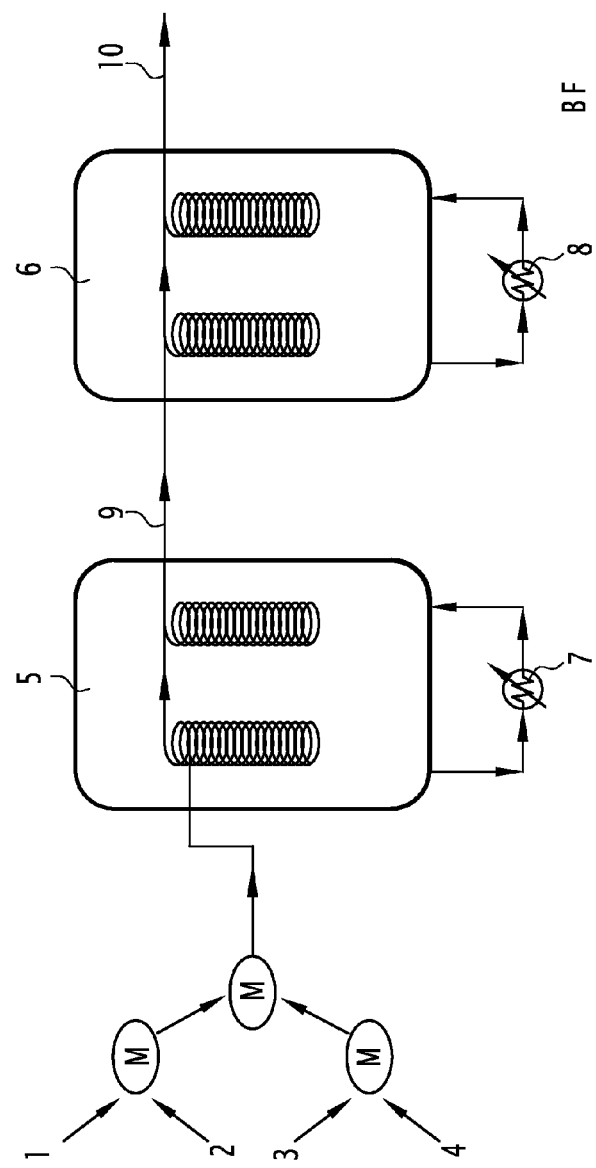

FIG. 3 shows an alternative of the device of FIG. 1.

The water (1) and the acid (2) on the one hand, and the amine (3) and the base (4) on the other hand, are introduced by means of mixers into the first tubular reactor (5) comprising heating means (7). The outlet of the first reactor and the inlet of the second tubular reactor (6) are connected to each other (9). The second reactor (6) is provided with heating means (8). The betaine aqueous solution (10) is recovered at the outlet of the reactor (6).

Figure 4:
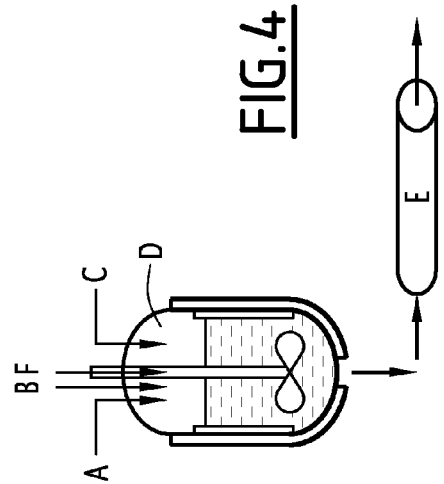

FIG. 4 shows another alternative of the device of FIG. 1.

This device is made up of a first agitated reactor (D) and a second tubular reactor (E). The different reagents (A, B, C) (acid, amine and base) are continuously introduced directly into the reactor (D) provided with agitating means (F).

FIG. 5 shows a detailed diagram of a tubular reactor.

The reagents (A) are introduced into the tubular reactor and the final products, in particular the betaine aqueous solution, are recovered at the outlet (B).

This reactor is provided with heating means (C) by means of a coolant.

EXAMPLES

General Description of the Method

The inventive method consisted of starting the pumps and adjusting them to the desired flow rate, and starting the heating bath so as to keep the reactors at temperature. Once the reactor was at temperature, we waited twice the total residence time, approximately 4 h, so as to stabilize the facility, and samples were done (in general, 4 spaced apart by 30 min), so as to verify the reproducibility of the measurements.

In the case of the implementation of two tubular reactors (R1) and (R2), the LDMA amine was mixed with potassium hydroxide containing 1% of betaine. The resulting mixture was then mixed with the monochloroacetic acid before entering the reactor (R1), then the reactor (R2).

In the case of the agitated reactor (R1) and tubular reactor (R2) combination, each component was injected separately into the agitated reactor. Each injection is comparable to a dip tube that releases the product close to the agitator so as to be well mixed. The outgoing flow flows by overflow and is collected in a small buffer tray that feeds a pump that discharges the liquid into the tubular reactor (R2).

The different reagents (amine, acid, base and water) were introduced into the reactors using Gilson chromatography pumps.

The mixers of the inventive device are micromixers made by IMM.

The tubular reactors that were used are chromatography tubes with an inner diameter of ⅛" or 1/16", and their length was adjusted as a function of the residence time. This tube was wound so as to obtain practically adjoining turns and a compact winding. This winding was enclosed in an enclosure in which a coolant circulates, making it possible to heat/cool the tubes. The circulation of the coolant and the monitoring of its temperature were done using a circulating thermostatic bath. Each enclosure contained two windings connected to each other by a three-way valve outside the enclosure, making it possible to perform samples or an injection.

Example 1

This example was done in a device made up of two tubular reactors (according to the diagram of FIG. 3).

Lauryldimethylamine (LDMA) was introduced with a flow rate (Q1) of 0.41 mL/min and potassium hydroxide (base) (at 30%) was introduced, in association with 1% of betaine, with a flow rate (Q2) of 0.26 mL/min. In parallel, the monochloroacetic acid (MCA) (at 28%) was introduced with a flow rate of (Q3) of 0.505 mL/min.

All of these reagents were introduced continuously into the first tubular reactor. The potassium hydroxide (30%) was also introduced with a flow rate (Q4) of 0.08 mL/min between the outlet of the first reactor and the inlet of the second reactor.

The first tubular reactor was kept at a temperature T1 equal to 95° C. and the residence time (t1) of the reagents was 41 minutes. The second tubular reactor was kept at a temperature T2 equal to 105° C. and the residence time (t2) of the reagents was 82 minutes.

A betaine aqueous solution was then obtained at the outlet of the second reactor comprising 0.4 wt % of residual MCA, 1.5 wt % of residual amine, and 1.6 wt % of glycolic acid.

Such an aqueous solution meets the specifications for use in an herbicidal composition.

Example 2

This example was done in the same device as that of example 1.

The conditions were identical in terms of flow rates, but the temperature conditions were different:

| Q1 (mL/min) | Q2 (mL/min) | Q3 (mL/min) | Q4 (mL/min) | T1 (° C.) | t1 (min) | T2 (° C.) | t2 (min) |
|---|---|---|---|---|---|---|---|
| 0.41 | 0.26 | 0.505 | 0.08 | 100 | 41 | 100 | 82 |

A betaine aqueous solution was then obtained at the outlet of the second reactor having the following characteristics:

| Residual MCA (wt %) | Residual amine (wt %) | Glycolic acid (wt %) |
|---|---|---|
| 0.26 | 2 | 1.6 |

Example 3

This example was done in the same device as that of example 1.

The conditions were identical in terms of flow rate, but the temperature conditions were different:

| Q1 (mL/min) | Q2 (mL/min) | Q3 (mL/min) | Q4 (mL/min) | T1 (° C.) | t1 (min) | T2 (° C.) | t2 (min) |
|---|---|---|---|---|---|---|---|
| 0.41 | 0.26 | 0.505 | 0.08 | 95 | 41 | 100 | 82 |

A betaine aqueous solution was then obtained at the outlet of the second reactor having the following characteristics:

| Residual MCA (wt %) | Residual amine (wt %) | Glycolic acid (wt %) |
|---|---|---|
| 0.56 | 1.8 | 1.4 |

Example 4

This example was done in the same device as that of example 1.

The conditions were identical in terms of flow rate, but the temperature conditions were different:

| Q1 (mL/min) | Q2 (mL/min) | Q3 (mL/min) | Q4 (mL/min) | T1 (° C.) | t1 (min) | T2 (° C.) | t2 (min) |
|---|---|---|---|---|---|---|---|
| 0.41 | 0.26 | 0.505 | 0.08 | 95 | 41 | 95 | 82 |

A betaine aqueous solution was then obtained at the outlet of the second reactor having the following characteristics:

| Residual MCA (wt %) | Residual amine (wt %) | Glycolic acid (wt %) |
|---|---|---|
| 0.7 | 2 | 1.3 |

Example 5

This example was done in the same device as that of example 1.

The conditions were identical in terms of flow rate, but the temperature and residence time conditions were different:

| Q1 (mL/min) | Q2 (mL/min) | Q3 (mL/min) | Q4 (mL/min) | T1 (° C.) | t1 (min) | T2 (° C.) | t2 (min) |
| --- | --- | --- | --- | --- | --- | --- | --- |
| 0.41 | 0.26 | 0.505 | 0.08 | 130 | 61 | 130 | 61 |

A betaine aqueous solution was then obtained at the outlet of the second reactor having the following characteristics:

| Residual MCA (wt %) | Residual amine (wt %) | Glycolic acid (wt %) |
| --- | --- | --- |
| 0 | 8.1 | 4.3 |

One can therefore see that when the temperatures of the reactors are highest (above 110° C.), betaine solutions are obtained with a high residual amine content.

Such solutions are not adapted for use in herbicidal compositions.

Example 6

This example was done in the same device as that of example 1, under the following conditions:

| Q1 (mL/min) | Q2 (mL/min) | Q3 (mL/min) | Q4 (mL/min) | T1 (° C.) | t1 (min) | T2 (° C.) | t2 (min) |
| --- | --- | --- | --- | --- | --- | --- | --- |
| 0.3 | 0.18 | 0.36 | 0.06 | 95 | 83 | 95 | 83 |

A betaine aqueous solution was then obtained at the outlet of the second reactor having the following characteristics:

| Residual MCA (wt %) | Residual amine (wt %) | Glycolic acid (wt %) |
| --- | --- | --- |
| 0.2 | 2.12 | 1.4 |

Example 7

This example was done in the same device as that of example 1, under the following conditions:

| Q1 (mL/min) | Q2 (mL/min) | Q3 (mL/min) | Q4 (mL/min) | T1 (° C.) | t1 (min) | T2 (° C.) | t2 (min) |
| --- | --- | --- | --- | --- | --- | --- | --- |
| 0.3 | 0.24 | 0.36 | 0 | 95 | 83 | 95 | 83 |

Thus, this example was done with intermediate potassium hydroxide addition (between the outlet of the first reactor and the inlet of the second reactor).

A betaine aqueous solution was then obtained at the outlet of the second reactor having the following characteristics:

| Residual MCA (wt %) | Residual amine (wt %) | Glycolic acid (wt %) |
| --- | --- | --- |
| 0 | 8.3 | 3.4 |

One can therefore see that the intermediate potassium hydroxide addition makes it possible to reduce the residual amine content in the final betaine solution.

The solutions obtained according to the method comprising such an addition have more interesting characteristics for use in herbicidal compositions.

Example 8

This example was done in the device of FIG. 4, i.e. a device comprising an agitated reactor and a tubular reactor.

Lauryldimethylamine (LDMA) was introduced with a flow rate (Q1) of 1.3 mL/min and the potassium hydroxide (base) (at 45%) was introduced with a flow rate (Q2) of 0.55 mL/min. In parallel, the monochloroacetic acid (MCA) (at 19.9%) was introduced with a flow rate (Q3) of 2.24 mL/min.

The first reactor (agitated reactor) was kept at a temperature T1 equal to 95° C. and the residence time (t1) of the reagents was 140 minutes. The second tubular reactor was kept at a temperature T2 equal to 95° C. and the residence time (t2) of the reagents was 60 minutes.

A betaine aqueous solution was then obtained at the outlet of the second reactor comprising 1.4 wt % of residual MCA, 0.9 wt % of residual amine, and 2.31 wt % of glycolic acid.

Example 9

This example was done in the same device as that of example 8, under the following conditions:

| Q1 (mL/min) | Q2 (mL/min) | Q3 (mL/min) | T1 (° C.) | t1 (min) | T2 (° C.) | t2 (min) |
| --- | --- | --- | --- | --- | --- | --- |
| 1.3 | 0.6 | 2.24 | 95 | 140 | 95 | 90 |

A betaine aqueous solution was then obtained at the outlet of the second reactor having the following characteristics:

| Residual MCA (wt %) | Residual amine (wt %) | Glycolic acid (wt %) |
| --- | --- | --- |
| 1.55 | 0.85 | 1.3 |

Example 10

This example was done in the same device as that of example 8, under the following conditions:

| Q1 (mL/min) | Q2 (mL/min) | Q3 (mL/min) | T1 (° C.) | t1 (min) | T2 (° C.) | t2 (min) |
| --- | --- | --- | --- | --- | --- | --- |
| 1.3 | 0.63 | 2.24 | 95 | 140 | 95 | 75 |

A betaine aqueous solution was then obtained at the outlet of the second reactor having the following characteristics:

| Residual MCA (wt %) | Residual amine (wt %) | Glycolic acid (wt %) |
| --- | --- | --- |
| 1.2 | 1.65 | 1.2 |

Example 11

This example was done in the same device as that of example 8, under the following conditions:

| Q1 (mL/min) | Q2 (mL/min) | Q3 (mL/min) | T1 (° C.) | t1 (min) | T2 (° C.) | t2 (min) |
|---|---|---|---|---|---|---|
| 0.65 | 0.32 | 1.12 | 95 | 275 | 95 | 40 |

A betaine aqueous solution was then obtained at the outlet of the second reactor having the following characteristics:

| Residual MCA (wt %) | Residual amine (wt %) | Glycolic acid (wt %) |
|---|---|---|
| 0.7 | 1.32 | 1.37 |

Such an aqueous solution meets the specifications for use in an herbicidal composition.

The invention claimed is:

1. A continuous method for preparing a betaine aqueous solution including a betaine with the following formula (I):

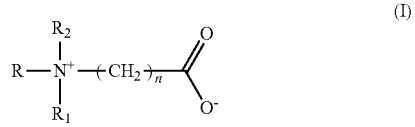

wherein:
n is equal to 1, 2 or 3;
$R_1$ represents a linear or branched alkyl group, comprising from 1 to 3 carbon atoms;
$R_2$ represents a linear or branched alkyl group, comprising from 1 to 3 carbon atoms;
R represents:
either a linear or branched hydrocarbonaceous chain, comprising from 3 to 30 carbon atoms;
or an -A-NH—CO—$R_3$ group,
$R_3$ representing a linear or branched hydrocarbonaceous chain, comprising from 3 to 30 carbon atoms; and
A representing a linear or branched divalent hydrocarbonaceous group comprising from 1 to 6 carbon atoms, possibly substituted by a hydroxyl group;
comprising the reaction of an amine of formula $NRR^1R^2$, R, $R^1$ and $R^2$ being as defined above, with an ω-halocarboxylic acid having formula X—$(CH_2)_n$—COOH, X representing a halogen atom and n being as defined above, in the presence of water and a base, and
wherein said method is carried out in a device made up of at least two consecutive reactors (R1) and (R2), the reactor (R2) being a tubular reactor.

2. The method according to claim 1, wherein $R_1$ represents a methyl group in the formula (I).

3. The method according to claim 1, wherein $R_2$ represents a methyl group in the formula (I).

4. The method according to claim 1, wherein R represents an alkyl group in the formula (I).

5. The method according to claim 1, wherein $R_3$ represents an alkyl group in the formula (I).

6. The method according to claim 1, wherein A is chosen from among the groups $CH_2$—$CH_2$—$CH_2$ or $CH_2$—CHOH—$CH_2$ in the formula (I).

7. The method according to claim 1, wherein the base is an alkali metal hydroxide.

8. The method according to claim 1, wherein the base is KOH or NaOH.

9. The method according to claim 1, comprising:
a step for introducing water, base, amine, and the ω-halocarboxylic acid at the inlet of the reactor (R1),
a reaction step between the amine and the ω-halocarboxylic acid in the reactor (R1) to obtain, at the outlet of the reactor (R1), an aqueous reactive mixture (M) comprising the betaine of formula (I), the amine and the ω-halocarboxylic acid;
a step for introducing the aqueous reactive mixture (M) at the inlet of the reactor (R2), to continue the reaction between the amine and the ω-halocarboxylic acid; and
a step for recovering a betaine aqueous solution (M') at the outlet of the reactor (R2) comprising at least 20 wt % by weight of the betaine of formula (I); and less than 2.5 wt % by weight of amine; and less than 1.5 wt % by weight of acid.

10. The method according to claim 9, wherein the betaine aqueous solution (M') comprises at least 30 wt % by weight of the betaine of formula (I).

11. The method according to claim 9, wherein the betaine aqueous solution (M') comprises less than 1.65 wt % by weight of amine.

12. The method according to claim 9, wherein the betaine aqueous solution (M') comprises less than 1 wt % by weight of acid.

13. The method according to claim 9, wherein during step a), the amine is introduced with the base on the one hand, and the acid is introduced with the water on the other hand.

14. The method according to claim 9, comprising an additional step b'), consisting of adding base into the reactive mixture (M) at the outlet of the reactor (R1) and before introducing said mixture into the reactor (R2).

15. The method according to claim 9, wherein a portion of the betaine aqueous solution (M') is recovered at the outlet of the reactor (R2) to be injected at the inlet of the reactor (R1) with the amine.

16. The method according to claim 1, wherein the outlet of the reactor (R2) is connected to one or more mixers comprising water, glycerin, anti-foaming agents or mixtures thereof, in order to prepare betaine aqueous solution-based in-line formulations.

17. The preparation method according to claim 1, wherein the temperature inside the reactor (R1) is comprised between 80° C. and 110° C.

18. The preparation method according to claim 1, wherein the temperature inside the reactor (R2) is comprised from 95° C. to 110° C.

19. The preparation method according to claim 1, wherein the pressure inside the reactor (R2) is comprised from 1 to 10 bars.

20. The preparation method according to claim 1, wherein the reactor (R1) is a tubular reactor.

21. The preparation method according to claim 1, wherein the residence time of the amine and the acid in the reactor (R1) is comprised from 30 minutes to 5 hours.

22. The preparation method according to claim 1, wherein the residence time of the amine and the acid in the reactor (R2) is from 30 minutes to 5 hours.

23. The preparation method according to claim 1, wherein the acid is monochloroacetic acid.

24. The preparation method according to claim 1, wherein the amine is lauryldimethylamine.

* * * * *